United States Patent [19]
Hammond

[11] Patent Number: 5,428,009
[45] Date of Patent: Jun. 27, 1995

[54] LIPOPEPTIDE DERIVATIVES

[75] Inventor: Milton L. Hammond, Sommerville, N.J.

[73] Assignee: Merck & Co., Inc., Rahway, N.J.

[21] Appl. No.: 553,496

[22] Filed: Jul. 16, 1990

[51] Int. Cl.$^6$ .......................... C07K 7/06; C07K 5/12; A61K 37/02
[52] U.S. Cl. ......................................... 514/11; 514/9; 530/317
[58] Field of Search ...................... 530/317; 514/9, 11

[56] References Cited

U.S. PATENT DOCUMENTS

| | | | |
|---|---|---|---|
| 4,293,490 | 10/1981 | Abbott et al. | 530/317 |
| 4,293,491 | 10/1981 | Debono et al. | 530/317 |
| 4,322,338 | 3/1982 | Abbott et al. | 530/317 |
| 4,791,100 | 12/1988 | Kramer et al. | 514/12 |
| 4,931,352 | 6/1990 | Fromfling et al. | 530/317 |

FOREIGN PATENT DOCUMENTS

| | | |
|---|---|---|
| 0431350A1 | 6/1991 | European Pat. Off. . |
| 0462531A2 | 12/1991 | European Pat. Off. . |
| WO82/00587 | 3/1982 | WIPO . |

OTHER PUBLICATIONS

W. Pache et al, 13th Int'l Congress Chemotherapy, PS 4.8/3, Part 115/31–32 Abstract No. 10.
Annual Reports in Medicinal Chemistry vol. 19, p. 131 (1984).

*Primary Examiner*—Robert J. Hill, Jr.
*Assistant Examiner*—S. G. Marshall
*Attorney, Agent, or Firm*—Elliott Korsen; Mark R. Daniel; Joseph F. DiPrima

[57] ABSTRACT

The present invention is directed to water-soluble derivatives of antibiotic lipopeptides. The derivatives have good solubility properties in aqueous medium, rendering them more useful as therapeutic agents.

7 Claims, No Drawings

LIPOPEPTIDE DERIVATIVES

The present invention is directed to a compound having the formula

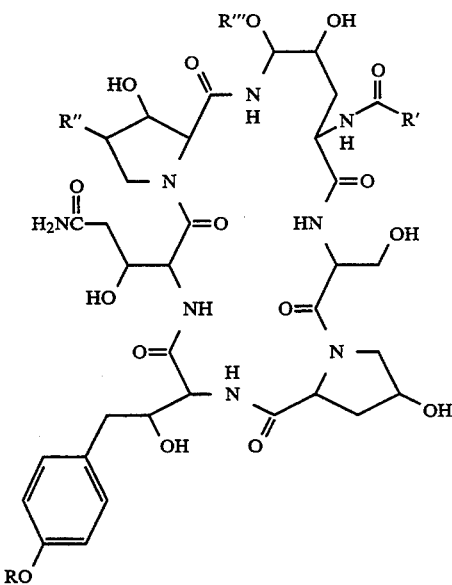

In this and succeeding formulas, R is an acyl, phosphono or sulfo radical which possesses a charged group at neutral pH; R' is a $C_5$–$C_{23}$ alkyl, $C_5$–$C_{23}$ alkenyl, $C_5$–$C_{23}$ alkynyl or aryl; R" and R''' are independently H or $CH_3$ and selected from those in which (1) R" is $CH_3$ and R''' is H; (2) R" and R''' are both H; and (3) R" and R''' are $CH_3$.

The alkyl, alkenyl and alkynyl groups may be either straight chain or branched. When alkenyl or alkynyl, from 1 to 3 unsaturated groups may be present. Especially preferred are $C_{13}$ to $C_{17}$ groups such as tridecyl, pentadecyl, 8,11-heptadecadienyl, 7-pentadecenyl, 10-heptadecenyl, 9, 11-dimethyltridecyl, and the like.

By the expression "aryl" is meant preferably phenyl or substituted phenyl. Substituents may be alkyl, alkyloxy, alkylthio, alkylamino. The carbon content of the alkyl is from 1 to 10. The preferred substituted aryl may be represented by

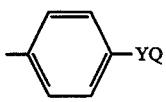

wherein Y is $CH_2$, S, O or NH and Q is $C_{6-10}$alkyl. A preferred member of this group is a radical in which Y is O, and Q is $C_8H_{17}$.

"Acyl, phosphono or sulfo radicals which possess a charged group at neutral pH" include those which may be an anion from an acid or a cation form of an amine base and may be further defined as follows:

(1) $PO_3AH$ wherein A is H, $C_1$–$C_6$ alkyl, phenyl or substituted phenyl in which the substituent is alkyl, alkylory, alkylthio, or alkylamino, or a cation salt thereof;

(2) $SO_3H$ or cation salt thereof;

(3) $COC_nH_{2n}CO_2H$ wherein n is 1 to 6, or a cation salt thereof;

(4) $CONAC_nH_{2n}CO_2H$ wherein A is as defined in (1), n is 1 to 6, or a cation salt thereof;

(5) $COOC_nH_{2n}CO_2H$ wherein n is 1 to 6, or a cation salt thereof;

(6) $CONA(CHB)CO_2H$ wherein A is as defined in (1) and B is a residue of an amino acid, or a cation salt thereof;

(7) $COCHBNR_1R_2$ wherein B is a residue of an amino acid, $R_1$ and $R_2$ independently are H, $C_1$–$C_6$ alkyl, and phenyl, or an acid addition salt thereof;

(8) $CONAC_nH_{2n}NR_1R_2$ wherein A is as defined in (1), $R_1$ and $R_2$ independently are as defined in (7), n is 2 to 6, and acid addition salts thereof;

(9) $COOC_nH_{2n}R_1R_2$ wherein $R_1$ and $R_2$ independently are as defined in (7), n is 2 to 6, and acid addition salts thereof;

(10) $COC_nH_{2n}NR_1R_2$ wherein $R_1$ and $R_2$ independently are as defined in (7), n is 1 to 6 and acid addition salts thereof; and

(11) COX where X is a leaving group.

The preferred group for R is

or a cation salt thereof.

By "cation salt" in (1)–(6) above is meant a salt of Li, K, Mg, Na, Ca, ($C_1$–$C_4$alkyl)ammonium.

By "acid addition salt" is meant pharmaceutically acceptable salts such as hydrochloride, hydrobromide, maleate, citrate, tartrate, acetate, succinate and the like.

By "neutral pH" is meant pH 6–8.

In referring to compounds hereinafter, the designation "A" following the word "Compound" will refer to a compound of formula (A) and the designations "1", "2" and "3" will indicate the nucleus. Thus, "Compound A-1" will refer to a compound in which R" is $CH_3$ and R''' is H; "Compound A-2" to a compound in which R" and R''' are H; "Compound A-3" to a compound in which R" and R''' are $CH_3$. R' and R will be designated by radical names following the number designation.

Preferred compounds are those in which (1) R" is $CH_3$ and R''' is H and (2>R" and R''' are both H, and in which R' is 9,11-dimethyltridecyl (DMTD), and R is phosphate (Phos) and which may be represented by the following formulas A-1a and A-2a, respectively. A-1a (=A-1-DMTD-Phos) and A-2a (=A-2-DMTD-Phos)

The compounds may be identified as (1) Compound A-l(DMTD-Phos) and (2) Compound A-2(DMTD-Phos).

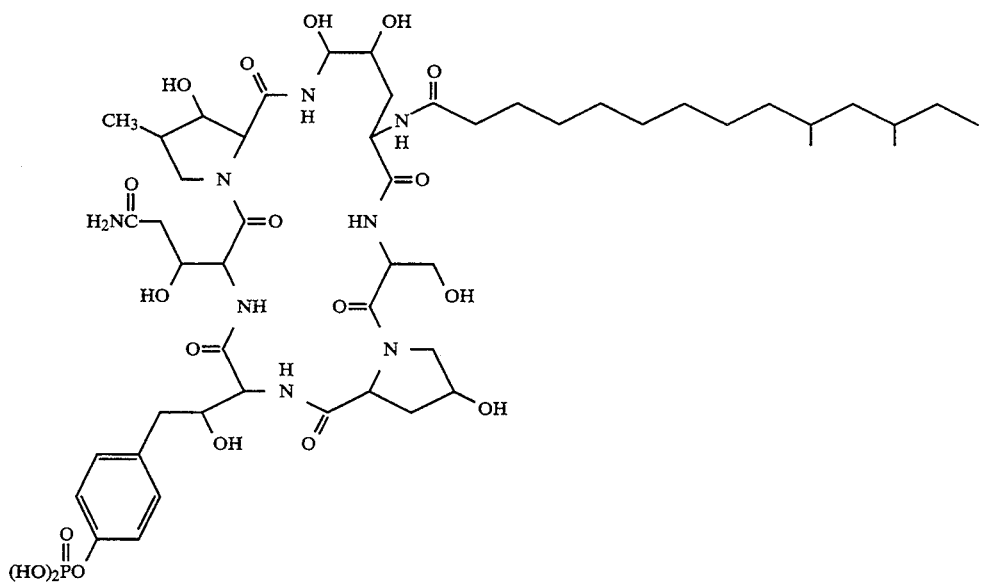

A-1(DMTD-Phos)

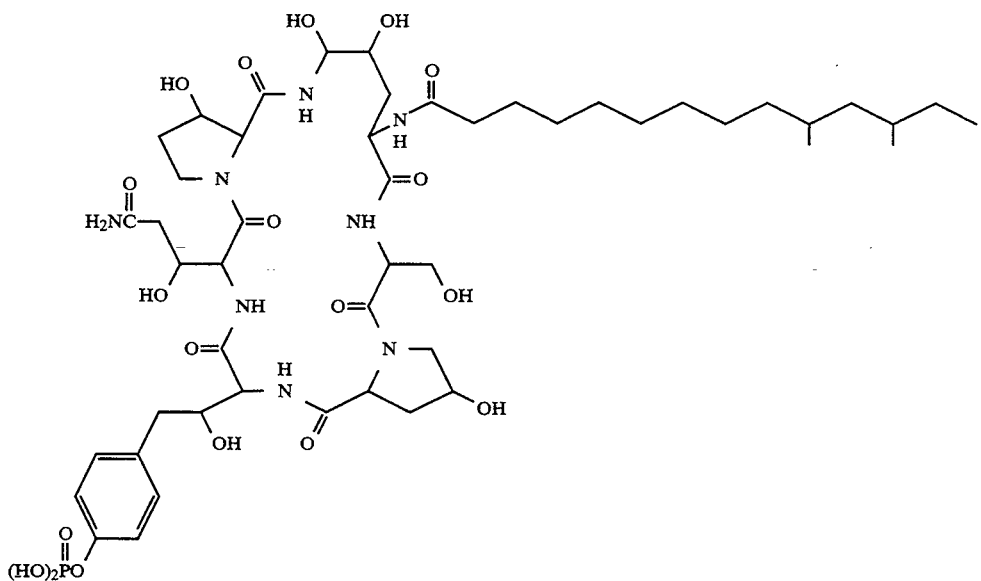

(A-2a)

The compounds of the present invention have antifungal and antiprotozoal activity. As antifungal agents, they are useful for the control of both filamentous fungi and yeasts. Among the filamentous fungi which may be controlled are Aspergillus species such as *Aspergillus flavus*, *Aspergillus fumigatus*, Neurospora species, Fusarium species, Alternaria species, and *Cochliobolus miyabeanus* and the like. They are also useful for the treatment of mycotic infections, especially those caused by the Candida organisms such as *C. albicans*, *C. parapsilosis* and the like. As antiprotozoal agents they may be useful for the control of organisms causing amebiasis such as *Entamoeba histolytica*, or malaria such as Plasmodium species, or other organisms such as Trypanosoma species, Toxaplasma species, Cryptosporidia and the like. They are especially useful for the prevention and or treatment of *Pneumocystis carinii* infections to which immune compromised patients are especially susceptible.

The compounds of the present invention which are generally white or light colored solids are derivatives of antibiotic lipopeptides. Unlike the parent compounds, the present compounds have good solubility properties in water and aqueous media. This property renders the compounds of the present invention more useful as therapeutic agents than the parent compound in many applications. Thus, they are adaptable to being used more readily in injectible compositions. Moreover, the compounds may have a prolonged duration of action.

The compounds of the present invention may be prepared from a lipopeptide having the formula (Z) by acylating at the phenolic hydroxyl and forming an ester link. The lipopeptide having formula Z are natural occurring or semi-synthetic lipopeptides obtained as subsequently described. The overall result may be represented by the following equation:

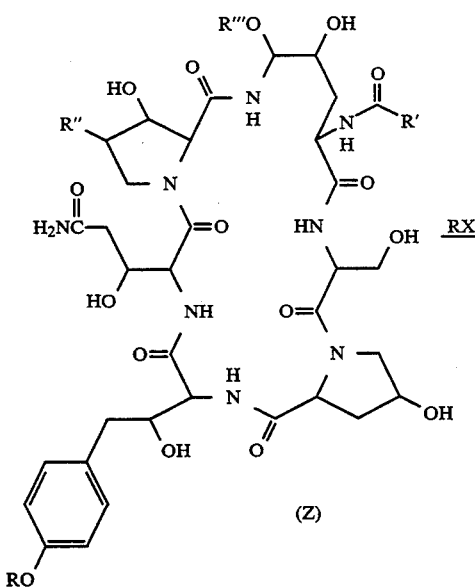

(Z)

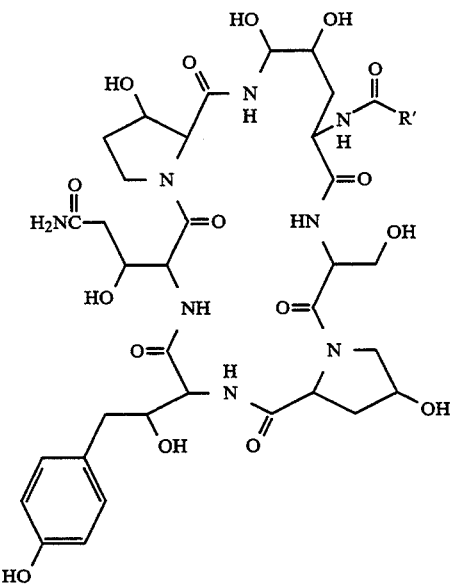

(Z-2)

(3) R″ and R‴ are CH₃

The individual nuclei for the lipopeptide starting material may be seen in the following formulas: (1) R″ is CH₃ and R‴ is H.

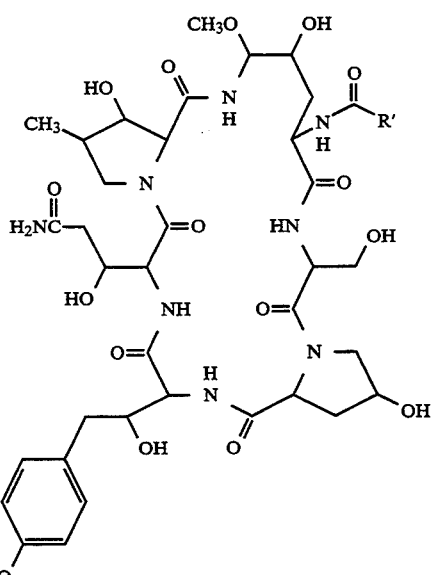

(Z-3)

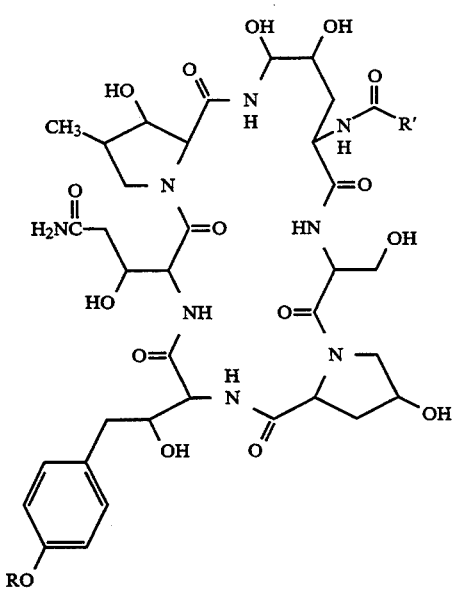

(Z-1)

(2) R″ and R‴ are H

Since the acyl group must have an ionizable group after completion of the acylation, the ionizable group is preferably protected during the acylation and the protecting group removed after completion of the acylation. Moreover, if R‴ is hydrogen, e.g., formula Z-1, it also may be protected during the acylation. Thus, the preparation of the desired products of the present invention may entail at least one protection/deprotection.

When R‴ in formula (Z) is methyl, as in formula Z-3, the compound may be acylated directly. When R‴ in Formula Z is hydrogen, as in nucleus Z-1 or Z-2, the first step is the etherification of the compound to form an ether, according to the following equation:

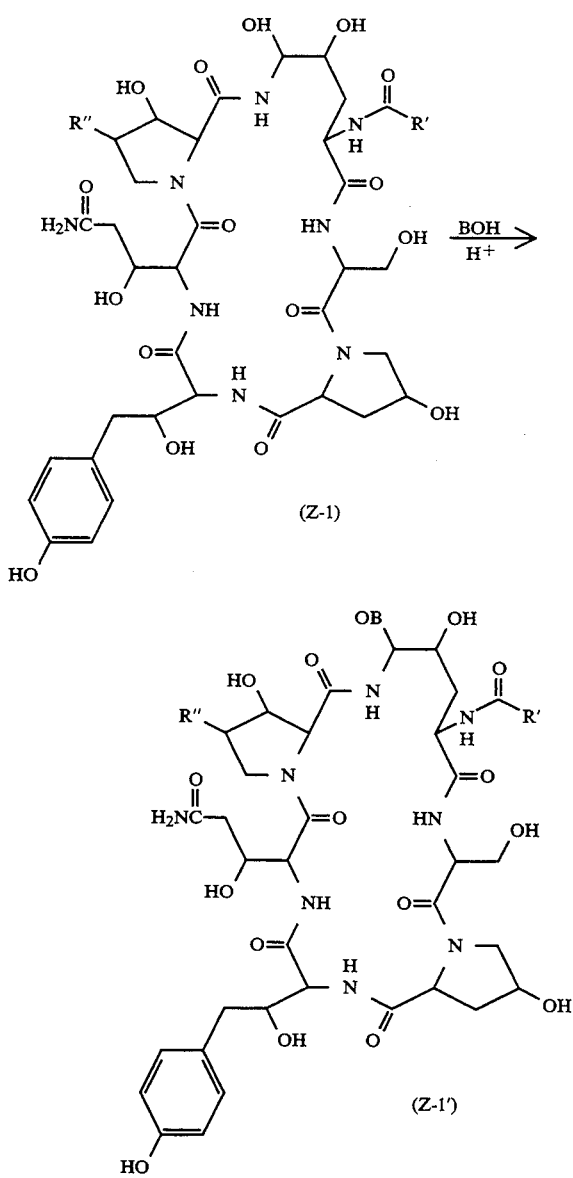

BOH is conveniently benzyl alcohol although other ether forming and readily cleavable alcohols may be employed, such as p-methoxybenzyl alcohol and 2,2,2-trichloroethanol.

The ether formation may be carried out by adding benzyl alcohol and p-toluenesulfonic acid to a solution or dispersion of the lipopeptide in a solvent and stirring at room temperature for from about 16 to 26 hours. The volatiles are then removed in vacuo and the ether product intermediate obtained as residue. The latter may be purified by preparative high performance liquid chromatography (HPLC). The resulting benzyl ether may be employed in the acylation.

The benzyl ether of a Z-1 lipopeptide or a Z-2 lipopeptide is then acylated. The acylation may be carried out by first adding dropwise with stirring at room temperature under an atmosphere of nitrogen, a 1M hexane solution of lithium hexamethyldisilazide (Aldrich) to a pyridine solution of the appropriate lipopeptide or benzyl ether of a lipopeptide and the resulting mixture stirred for 10 to 15 minutes. Then, a solution of RX is added quickly and the resulting mixture stirred from 15 to 60 minutes to obtain the R ester of the lipopeptide or of the benzyl ether of the lipopeptide. The volatiles are then removed in vacuo to obtain the crude ester as a residue. The latter is then purified by preparative high performance liquid chromatography (HPLC) using $H_2O/CH_3CN$ as eluting agent. The eluant fractions having the desired retention time are lyophilized to obtain the desired intermediate ester.

The RX may by any of the compounds which would embraced in the formula using the aforecited definitions for R and for X.

The preferred derivatives of the lipopeptides are phosphate esters. When the ester is a phosphate ester, the preferred esterification intermediate is a dibenzyl phosphate ester. The dibenzyl phosphate ester may be prepared by adding a solution of tetrabenzylpyrophosphate in pyridine to a stirred mixture of lipopeptide or benzyl ether of lipopeptide and lithium hexamethyldisilazide to obtain the dibenzylphosphate ester of the lipopeptide.

The acid or acid salt of the ester may be obtained by low pressure hydrogenolysis of the dibenzylphosphate ester of the lipopeptide or benzyl ether of the lipopeptide. During hydrogenolysis both the benzyl of the phosphate ester and the benzyl of the benzyl ether are cleaved to obtain a phosphate ester of the lipopeptide.

If it is desired to obtain the ultimate ester as its water-soluble salt, the hydrogenolysis may be carried out under mildly alkaline conditions and the desired product recovered as its salt. The free acid may be obtained by controlled acidification.

In one preferred method of carrying out the hydrogenolysis, a solution of dibenzylphosphate in aqueous ethanol is hydrogenated at 1 atmosphere over Pd-C catalyst for 10 to 20 hours whereupon the benzyl groups of the phosphate ester are removed to obtain Compound I as an acid. If the starting lipopeptide is a benzyl ether, the benzyl of the ether is also removed. When it is desired to obtain the ultimate ester product as a salt of the acid, the hydrogenolysis medium may be made mildly alkaline with alkali metal bicarbonate and the salt recovered directly. Alternatively, the free acid may be recovered on hydrogenolysis and subsequently converted to the salt by methods known in the art.

When R is a sulfonic acid ester or carboxylic acid ester, the reaction may be carried out in a manner similar to that described for phosphoric acid ester. R may also be a radical in which the charged group at a neutral pH is an ammonium group formed preferably from the amino group of an amino acid which has been esterified at the phenolic hydroxyl.

In certain instances the preferred R may be a sulfate ester as defined under (2). In these cases the sulfate ester may be prepared directly by treatment of a solution of the lipopeptide or lipopeptide benzyl ether in pyridine with sulfur trioxide pyridine complex to produce the pyridinium sulfate ester. If the free acid is desired it may be obtained by acidification with a strong acid such as hydrochloric acid followed by purification using a "Zorbax" C8 reverse phase HPLC column as stationary phase. If the lipopeptide benzyl ether is employed the benzyl ether may be removed by hydrogenolysis as described above.

When RX is a carboxylic acid derivative the preferred reagents for acylation are the carboxylic acid chlorides and anhydrides. The incipient charged group if it is to be a carboxylic acid salt may preferably be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in one preferred esterification, the lipopeptide or lipopeptide benzyl ether in pyridine containing 4-dimethylaminopyridine as catalyst is treated with the symmetrical anhydride of the carboxylic acid to produce the carboxylic ester. Deprotection preferably by hydrogenolysis of the benzyl ester, if the charged group is to be an acid, or by hydrogenolysis of the benzyloxycarbonyl group, if the charged group is to be an amine, then releases carboxylic acid or amine respectively. If the charged group is to be an acid then the hydrogenolysis may be carried out under mildly alkaline conditions to obtain the water soluble salt directly. Conversely if the charged group is to be amine base the hydrogenolysis may be carried out under mildly acidic conditions to obtain the water soluble ammonium salt directly.

It certain instances such as in definitions (4),(6), and (8) above, the ester linkage forms a portion of a carbamate. In those cases where A as defined in (1) above is hydrogen, the preferred reagent for acylation is the isocyanate. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in a preferred esterification, the lipopeptide or lipopeptide benzyl ether in pyridine containing 4-dimethylaminopyridine is treated with the isocyanate to produce the carbamate. Deprotection may then proceed in a preferred case by hydrogenolysis as described above to release the charged group. In those instances in which A is other than hydrogen as defined in (1) above, a different procedure must be used. In these cases a preferred method involves initial formation of a reactive carbonate. Thus, a solution of the lipopeptide or lipopeptide benzyl ether in pyridine containing 4-dimethylaminopyridine is treated with p-nitrophenyl chloroformate and in this way the mixed p-nitrophenyl carbonate is prepared. In a separate step the p-nitrophenyl carbonate is converted to the desired carbamate. Treatment of the p-nitrophenyl carbonate in dimethylformamide with a secondary amine provides the protected carbamate. Deprotection may then proceed in a preferred case by hydrogenolysis as described above to unveil the charged group and provide the compounds defined (4), (6) and (8) above where A is other than hydrogen.

When compounds with radicals such as those described in (5) and (9) above are desired, the ester link forms a portion of a carbonate. In these cases, the preferred reagents for acylation are the chloroformares. The incipiently charged group if it is to be a carboxylic acid salt preferably may be protected during the acylation reaction as a benzyl ester or other easily removed esters such as 2,2,2-trichloroethyl esters or allyl esters. If the incipiently charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in a preferred esterification, the lipopeptide or lipopeptide benzyl ether in pyridine containing 4-dimethylaminopyridine is treated with the chloroformate to produce the carbonate. Deprotection may then proceed in a preferred case by hydrogenolysis as described above to release the charged group.

The compounds of the present invention are useful for inhibiting or alleviating *Pneumocystis carinii* infections. In such use, Compound I or a composition containing Compound I is administered in a therapeutically effective or inhibitory amount to subjects infected with or susceptible to being infected with *Pneumocystis carinnii*.

The efficacy of the compounds of the present invention for therapeutic or anti-infective purposes may be determined in studies on immunosuppressed rats.

In a representative study, Sprague-Dawley rats (weighing approximately 250 grams) are immunosuppressed with dexasone in the drinking water (2.0 mg/L) and maintained on a low protein diet for five weeks to induce the development of pneumocystis pneumonia from a latent infection. Before drug treatment, two rats are sacrificed to confirm the presence of *Pneumocystis carinii* pneumonia (PCP). Then, six rats (weighing approximately 150 grams) are injected twice daily for four days intravenously (I.V.) via the tail vein with Compound A-1a in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic analysis of stained slides. Compound A-1a is useful in eliminating *P. carinii* cysts.

In another study, rats are injected intraperitoneally (I.P.) twice daily for four days, the animals are sacrificed, the lungs removed and processed, and the extent of disease determined by microscopic analysis of stained slides.

The compounds of the present invention are active against many fungi and particularly against Candida species. The antifungal properties may be illustrated with the minimum fungicidal concentration (MFC) determinations against certain Candida organisms in a microbroth dilution assay carried out in a Yeast Nitrogen Base (Difco) medium with 1% dextrose (YNBD). In carrying out the assay, Compound A-1a and A-2a are solubilized in 10% dimethyl sulfoxide (DMSO) and diluted to 2560 $\mu$g/ml. The compounds are then diluted to 256 $\mu$g/ml in YNBD. 0.15 ml of the suspension is dispensed to the top row of a 96-well plate (each well containing 0.15 ml of YNDB) resulting in a drug concentration of 128 $\mu$g/ml. Two-fold dilutions are then made from the top row to obtain final drug concentrations ranging from 128 to 0.06 $\mu$g/ml.

The yeast cultures, maintained on Sabouraud dextrose agar are transferred to YM broth (Difco) and incubated overnight at 35° C. with shaking (250 rpm). After incubation, each culture is diluted in sterile water to yield a final concentration of $1-5 \times 10^6$ colony forming units (CFU)/ml.

96-well microplates are inoculated using a MIC-2000 (Dynatech) which delivers 1.5 µl per well yielding a final inoculum per well of $1.5-7.5 \times 10^3$ cells. The microplates are incubated at 35° C. for 24 hours. The minimum inhibitory concentrations (MICs) are recorded as the lowest concentrations of drug showing no visible growth.

After recording the MIC, the plates were shaken to resuspend the cells. Thereafter, 1.5 µl samples from the wells in the 96-well microplate were transferred to a single well tray containing Sabouraud dextrose agar. The inoculated trays are incubated 24 hours at 28° C. and then read. The MFC is defined as the lowest concentration of drug showing no growth or less than 4 colonies per spot. Compounds A-1a and A-2a may be employed at concentrations of about 32 µg/ml or less to control *C. albicans, C. tropicalis* or *C. parapsilosis*.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), nasal administration, or insufflation. The compositions may be prepacked by intimately mixing Compound A with the components suitable for the medium desired.

When the compound is for antifungal use any method of administration may be used. For treating mycotic infection oral administration is frequently preferred. When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound A also may be formulated in therapeutic compositions for intravenous or intraperitoneal injection and may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and-/or dispersing agents. Buffering agents as well as additives such as saline or glucose may be added to make the solutions isotonic. The drug also may be solubilized in alcohol/propylene glycol or polyethylene glycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The preferred delivery system for inhalation is a metered dose inhalation (MDI) aerosol, which may be formulated as a suspension or solution of Compound A in suitable propellants, such as fluorocarbons or hydrocarbons.

Although the compounds of the present invention may be employed as tablets, capsules, topical compositions, insufflation powders, suppositories and the like, the advantage of the derivatives of the present invention over the parent lipopeptide is in their water solubility. Hence, the compounds of the present invention are most effectively utilized in injectible formulations and also in liquid compositions suitable for aerosol sprays.

Compound A also may be employed against a broad spectrum of yeasts and filamentous fungi (molds). For non-medical application, the product of the present invention, may be employed in compositions in an inert-carrier which includes finely divided dry or liquid diluents, extenders, fillers, conditioners and excipients, including various clays, diatomaceous earth, talc, and the like, various organic liquids such as lower alkanols, for example, ethanol and isopropanol, or kerosene, benzene, toluene and other petroleum distillate fractions or mixtures thereof. However, as with medical applications, the compounds are best utilized in aqueous compositions.

The following examples illustrate the invention but are not to be construed as limiting:

EXAMPLE I

1-[4,5-dihydroxy-N2-(10,12-dimethyl-1-oxotetradecyl-)ornithine]-2-serine-4-[3-hydroxy-4'-O-phosphoryl-homotyrosine]-5-[3-hydroxyglutamine]-echinocandin C disodium salt (I)

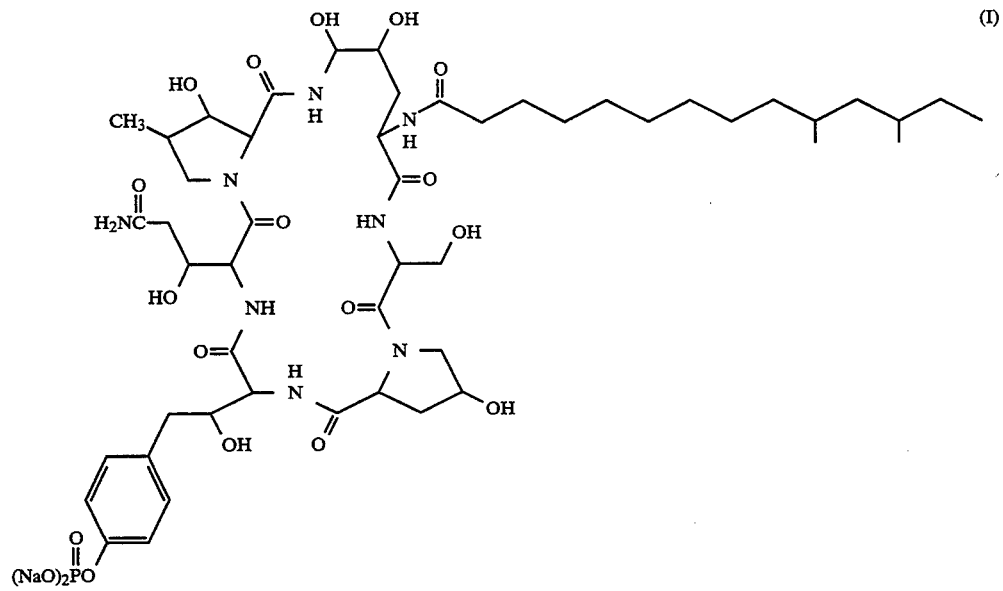

(I) (Compound A-1a)

Part A. Benzyl Ether

1-[4-hydroxy-5-benzyloxy-N2-(10,12-dimethyl-1-oxetetradecyl)-ornithine]-2-serine-5-[3-hydroxyglutamine]-echinocandin C (Ia)

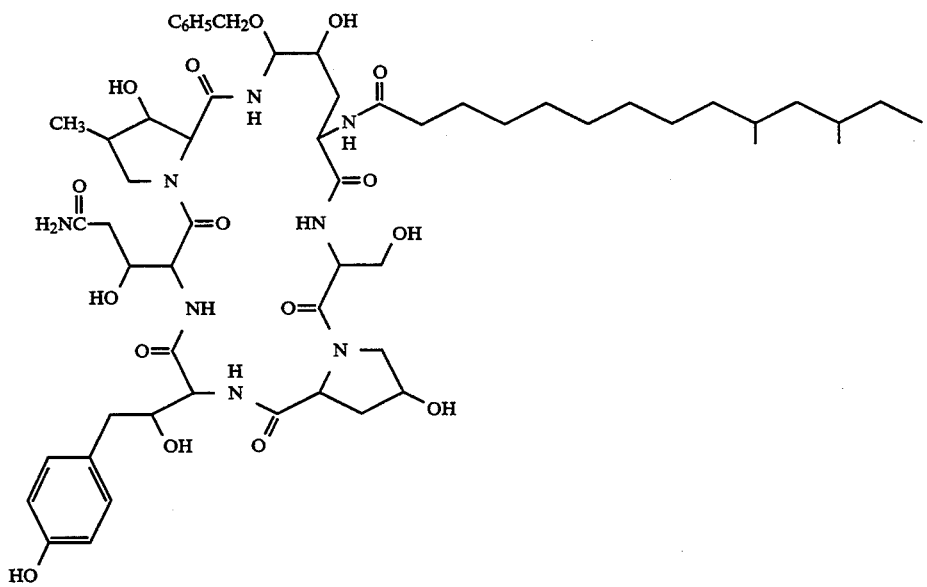

(Ia)

335 mg of 1-[4,5-dihydroxy-N2-(10,12-dimethyl-1-oxotetradecyl)-ornithine]-2-serine-5-(3-hydroxyglutamine)-echinocandin C (Compound Z-1(DMTD)) is suspended in 7 milliliters of tetrahydrofuran and to the suspension is added 0.68 milliliter of benzyl alcohol and 7 milligrams of p-toluenesulfonic acid. The mixture remains heterogeneous; 3 milliliters of dimethylformamide is added and the resulting solution stirred for 24 hours at room temperature. At the end of this period, the volatiles are removed in vacuo to obtain a residue which is purified by preparative HPLC (21.2×250 mm C8 "Zorbax" (DuPont)) eluting with water/acetonitrile (40/60) at 10 ml/min. and collecting 15 milliliter fractions. The appropriate fractions (as determined by UV at 210 nm) are combined and lyophilized to obtain the benzyl ether intermediate (Ia).

Part B. Dibenzylphosphate Ester

1-[4-hydroxy-5-benzyloxy-N2-(10,12-dimethyl-1-oxotetradecyl)-ornithine]-2-serine-4-[3-hydroxy-4'-O,O-dibenzyl-phosphoryl-homotyrosine]-5-[3-hydroxyglutamine ]echinocandin C (Ib)

Part C. Preparation of Sodium Salt Phosphate Ester (Hydrogenolysis of Dibenzylphosphate)

62 milligrams (0.0438 mmole) of the intermediate (Ib) above obtained is dissolved in 6 milliliters of water/ethanol (1:1) and to it is added a solution of 7.4 mg

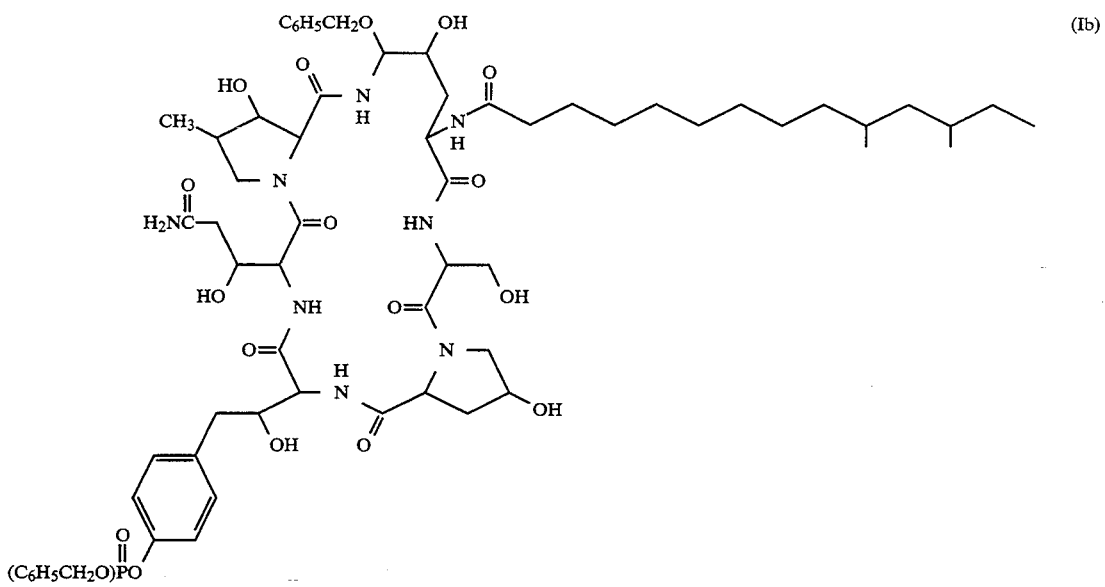

88 milligrams (0,076 mmole) of the benzyl ether of Z-i(DMTD) (formula Ia) is dissolved in 1.5 milliliters of dry pyridine under a nitrogen atmosphere. 152 microliters (0–152 mmole) of a 1M solution in hexane of lithium hexamethyldisilazide (Aldrich) is added dropwise and stirred for 10 minutes at room temperature. Then, a solution of 49 milligrams (0.0912 mmole) of tetrabenzylpyrophosphate in 0.5 milliliter of pyridine is added quickly and the resulting solution stirred for 15 minutes. Then, the volatiles are removed in vacuo to obtain a residue. The residue is purified by preparative HPLC (9.4×250 mm C8 "Zorbax"), eluting with water/acetonitrile (35/65) and collecting 4.5 ml fractions. The appropriate fractions (as determined by UV at 210 nm) are lyophilized to obtain the desired dibenzyl phosphate intermediate (Ib).

(0.0875 mmole) of sodium bicarbonate in distilled water. Next 60 milligrams of 10% Pd-C was added and the mixture stirred under 1 atmosphere of hydrogen at room temperature for 7 hours. The mixture was then filtered through a 0.2 micron filter, washed with 1:1 ethanol/water and concentrated on a rotary evaporator. The residue was lyophilized to obtain the product as a white solid. The molecular weight of the disodium salt is 1172.

EXAMPLE II

1-[4,5-dihydroxy-N2-(10,12-dimethyl-1-oxo-tetradecyl)-ornithine]-2-serine-4-[3-hydroxy-4'-0-phosphoryl-homotyrosine
]-5-[3-hydroxyglutamine]-6-[3-hydroxyproline]echinocandin C disodium salt

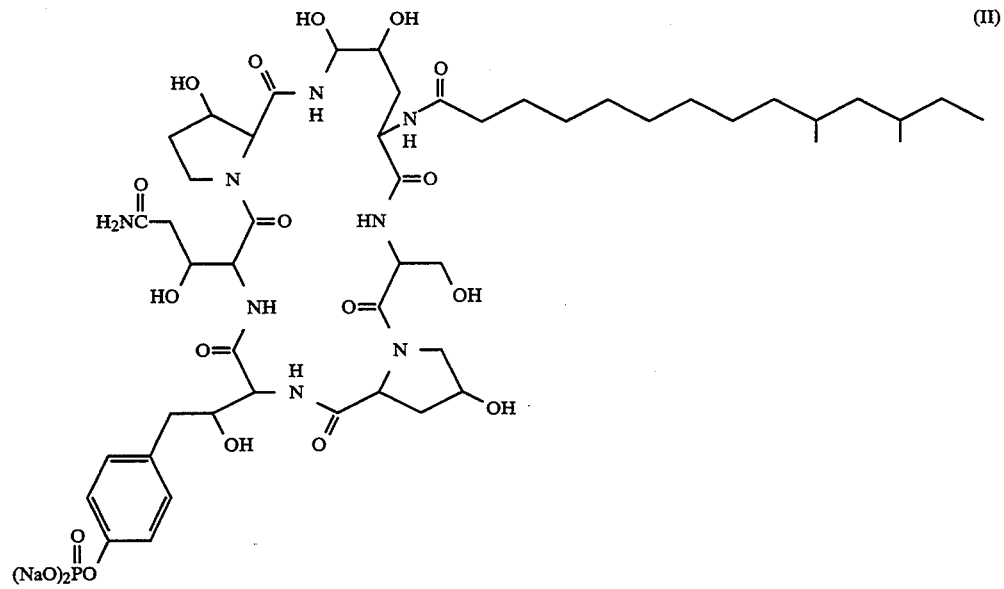

(II) (Compound A-2a)

Part A. Dibenzylphosphate Ester

1-[4-hydroxy-5-benzyloxy-N2-(10,12-dimethyl-1-oxotetradecyl)-ornithine]-2-serine-4-[3-hydroxy-4'-O,O-dibenzylphosphoryl-homotyrosine]-5-[3-hydroxyglutamine]-6-[3-hydroxy-proline]echinocandin C

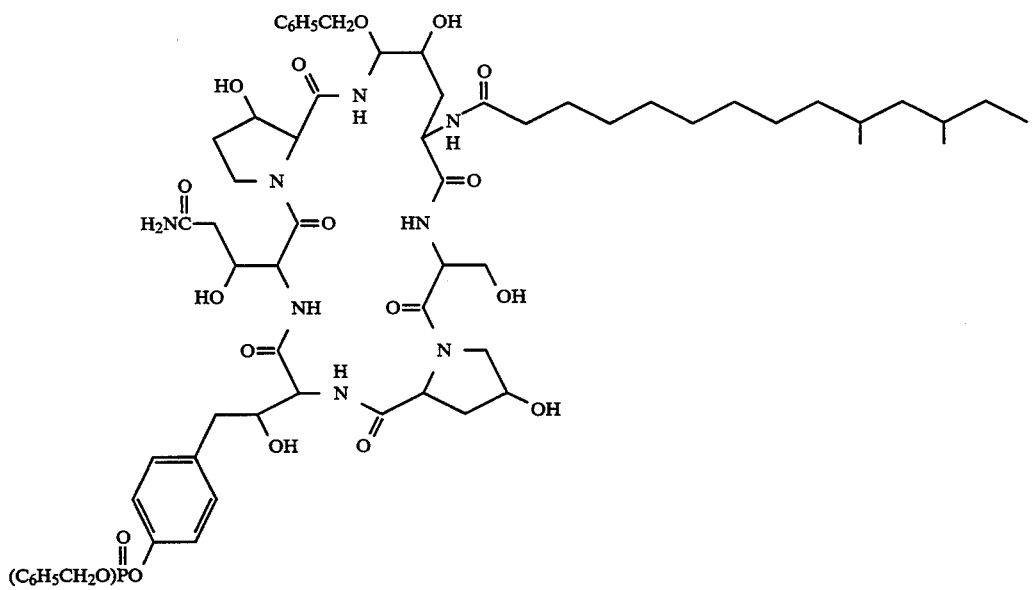

(IIb)

To a solution of 1 gram (0.956 mmole) of 1-[4-hydroxy-5-benzyloxy-N2-(10,12-dimethyl-1-oxotetradecyl)-ornithine]-2-serine-5-[3-hydroxyglutamine]-6-[3-hydroxyproline]-echinocandin C in 25 ml of dry pyridine is added dropwise with stirring under an atmosphere of nitrogen at room temperature, 1.43 milliliters of a 1M solution in hexane of lithium hexamethyldisilazide. The resulting solution is stirred at room temperature for 10 minutes and to it is rapidly added a solution of 566 milligrams (1.05 mmole) of tetrabenzylpyrophosphate in 5.0 milliliters of pyridine. The resulting solution is stirred for one hour after which an additional 100 milligrams of pyrophosphate is added as a solid. The volatiles are removed in vacuo to obtain a residue. A HPLC analysis of the latter on C8 "Zorbax" employing water/acetonitrile (30/70) at 2 ml/min. shows the reaction to be nearly complete with the formation of the compound of Claim 1.

Part B. Phosphoric Acid Ester of Z-2

1-[4,5-dihydroxy-N2-[10,12-dimethyl-1-oxotetradecyl-)ornithine]-2-serine-4-[3-hydroxy-4'-O-phosphoryl-homotyrosine]-5-[3-hydroxyglutamine]-6-[3-hydroxy-proline]echinocandin C disodium salt The dibenzyl phosphate prepared as described in Part A (470 milligrams, 0.36 mmol) is dissolved in 20 milliliters of absolute ethanol. To it is added a solution of 60.5 milligrams (0.72 mmol) of sodium bicarbonate in 10 milliliters of water followed by 157 milligrams of 10% Pd-C and the mixture stirred under 1 atmosphere of hydrogen at room temperature for four hours. At the end of this period, the mixture is filtered, washed with 1:1 ethanol/water and concentrated. The product is purified in four units by preparative HPLC (21.2×250 mm C8 Zorbax, water/acetonitrile (55/45) at 12 ml/min, 4.8 milliliter fractions) and the appropriate fractions concentrated and lyophilized to obtain the desired product. The molecular weight of the disodium salt is 1158.

EXAMPLE III

1-[4-hydroxy-5-methoxy-N2-(10,12-dimethyl-1-oxotetradecyl)ornithine]-2-serine-4-[3-hydroxy-4'-O-(2-N-methylcarbamoylacetic acid)-homotyrosine]-5-[3hydroxyglutamine]echinocandin C

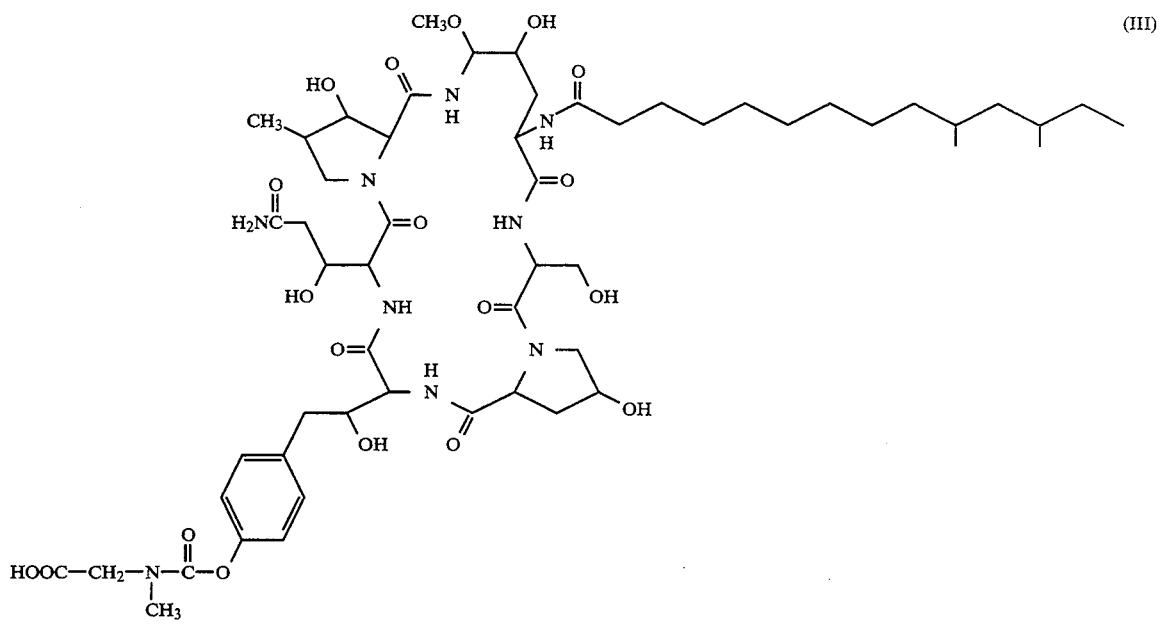

(III)

Part A.
1-[4-hydroxy-5-methoxy-N2-(10,12-dimethyl-1-oxo-tetradecyl)-ornithine]-2-serine-4-[3-hydroxy-4'-p-nitrophenylcarbonate-homotyrosine]-5-[3-hydroxyglutamine]echinocandin C

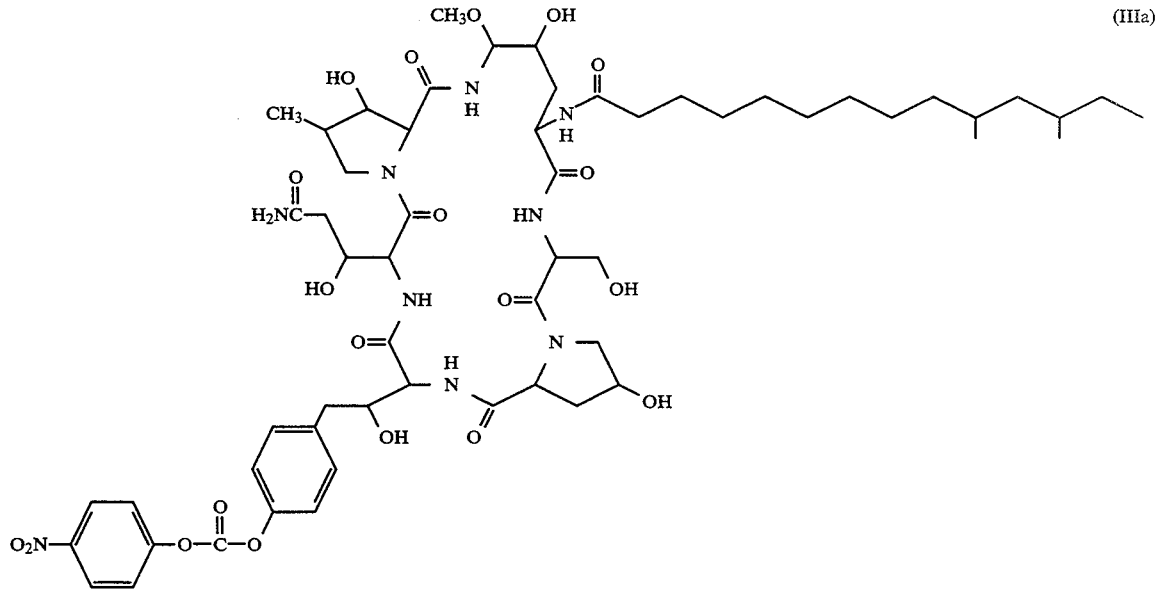

(IIIa)

To a solution of Z-3 (DMTD) 0.248g (0.234 mmol) in 2.5 ml of dry pyridine is added sequentially 31 mg (1.1 eq) 4-dimethylaminopyridine and 52 mg (1.1 eq) of p-nitrophenyl chloroformate and the mixture allowed to stir at room temperature for 20 hours. At the end of this period, the mixture is concentrated in vacuo and the residue dissolved in water/acetonitrile and thereafter purified by preparative reverse phase chromatography, eluting with water/acetonitrile. The fractions containing the desired product are concentrated in vacuo to remove the acetonitrile and then lyophilized to obtain purified p-nitrophenyl carbonate ester.

Part B.
1-[4-hydroxy-5-methoxy-N2-(10,12-dimethyl-1-oxo-tetradecyl)-ornithine]-2-arginine-4-[3-hydroxy-4'-O-(2-N-methylcarbamoylacetic acid)-homotyrosine]-5-[3-hydroxyglutamine]echinocandin C To a solution of 100 mg (0.081 mmol) of the p-nitrophenyl carbonate in 1 ml of dry dimethylformamide is added 15 mg (1.1 eq) of benzyl safcosine and the mixture allowed to stir at room temperature for 20 hours. The crude reaction mixture is concentrated in vacuo, the residue dissolved in water/acetonitrile and purified by reverse phase chromatography on "Zorbax" C8 column and eluted with acetonitrile/water. The fractions containing the desired intermediate is concentrated in vacuo to remove the acetonitrile and then lyophilized to obtain a purified benzyl ester.

The ester is dissolved in 15 ml of absolute ethanol and to the solution is added 15 mg of 10% Pd-C and stirred at 1 atmosphere for 5 hours. At the end of this period, the mixture is filtered and the filtrate concentrated to obtain the desired product (III). The product is purified on preparative HPLC employing water/acetonitrile. The molecular weight is 1177.

EXAMPLE IV

1-[4,5-dihydroxy-N2-(10,12-dimethyl-1-oxotetradecyl)ornithine]-2-serine-4-[3-hydroxy-4'-O-(2-carbamoyl acetic acid homotyrosine]-5-[3-hydroxyglutamine]echinocandin C

Part A. Benzyl Ether

In a manner similar to that described in Example I, 0.68 ml of benzyl alcohol and 7 mg of p-toluenesulfonic acid are added to a solution of 350 mg of Compound Z-1(DMTD) in a mixture of 7 ml of tetrahydrofuran and 3 ml of dimethylformamide and the mixture stirred at room temperature for 24 hours. At the end the volatiles are removed in vacuo to obtain a residue which is purified on a preparative HPLC column using water-/acetonitrile (40/60) as eluant. The appropriate fractions are combined and lyophilized to obtain benzyl ether of Z-1(DMTD).

Part B. Benzyl Ester

1-[4-hydroxy-5-benzyloxy-N2-(10,12-dimethyl-1-oxotetradecyl)ornithine]-2-serine-4-[3-hydroxy-4'-O-(benzyl 2-carbamoylacetate)-homotyrosine]-5-[3hydroxyglutamine]echinocandin C To a solution of 28 milligrams (0.027 mmol) of the benzyl ether of Z-1 (DMTD) in 200 microliters of dry pyridine was added sequentially 5 milligrams (0.041 mmol) of 4-dimethylaminopyridine and 5.2 milligrams (1 eq) of benzyl 2-isocyanatoacetate in 100 microliters of pyridine and the mixture stirred at room temperature under nitrogen for one hour. The mixture is concentrated in vacuo and then dissolved in 25/75 acetonitrile/water. At this time HPLC assay showed only partial completion of reaction so another 5 milligrams of benzyl 2-isocyanatoacetate was added and stirred to obtain the desired product. The product was isolated by preparative HPLC using water/acetonitrile as eluant at 10 ml/min and collecting 8 milliliter fractions to obtain the desired product.

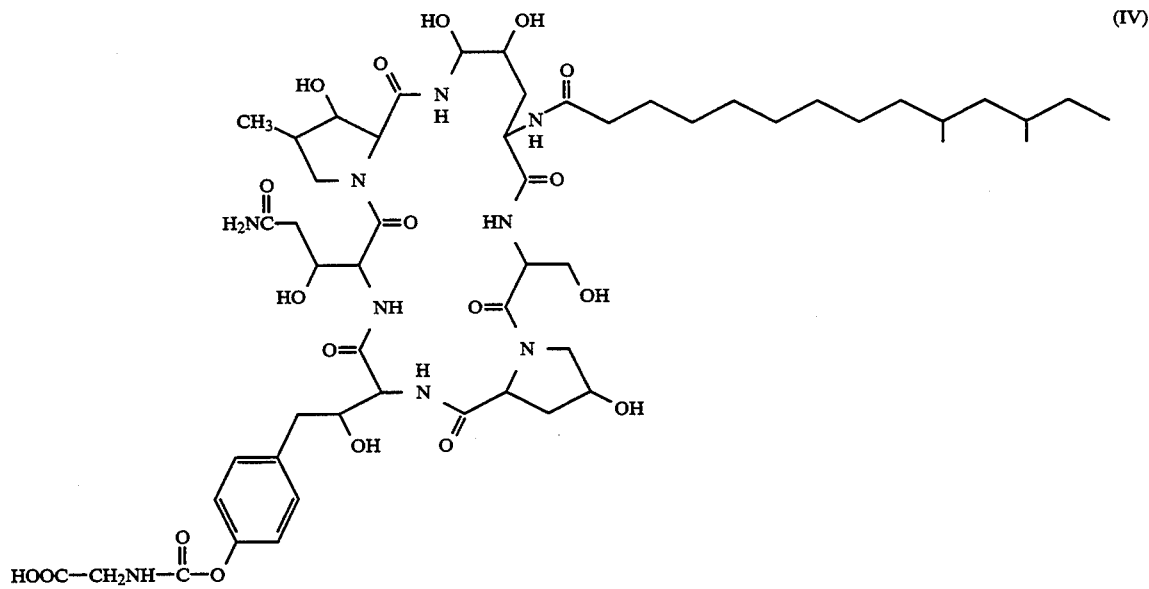

(IV)

Part C

1-[4,5-dihydroxy-N2-(10,12-dimethyl-1-oxotetradecyl-)ornithine]-2-serine-4-[3-hydroxy-4'-O-(2-carbamoyl acetic acid-homotyrosine]-5-[3-hydroxyglutamine]echinocandin B 7 milligrams of the benzyl ester obtained in Part B was dissolved in 2.5 milliliters of 50/50 water/ethanol containing 0.50 milligrams of sodium bicarbonate. An equal weight of Pd-C was added and the reaction mixture was stirred at room temperature over 1 atmosphere of hydrogen for one hour. At the end of this time the mixture was filtered and the ethanol vaporized and the concentrate lyophilized to obtain the product of formula (IV) as a solid having a molecular weight of 1163.

EXAMPLE V

1-[4,5-dihydroxy-N2-(10,12-dimethyl-1-oxotetradecyl-)ornithine]-2-serine-4-[3-hydroxy-4'-O-(malonic acid)-homotyrosine]-5-[3-hydroxyglutamine]-6-[3-hydroxyproline]echinocandin C and the mixture stirred at room temperature. The reaction mixture is concentrated in vacuo, the residue dissolved in water/acetonitrile and purified by preparative reverse phase chromatography. Fractions containing the desired material are concentrated in vacuo to remove the acetonitrile and then lyophilized to obtain the benzyl ester, 1-[4-hydroxy-5-benzyloxy-N2-(10,12-dimethyl-1-oxotetradecyl)-ornithine]-2-serine-4-[3-hydroxy-4'-O-(benzylmalonate)homotyrosine]-5-[3-hydroxyglutamine]-6-[3hydroxyproline]echinocandin C.

The benzyl ester is then subjected to hydrogenolysis in ethanol over 10% palladium on carbon catalyst at room temperature for about 8 hours. Then the catalyst is filtered off and the filtrate concentrated to obtain 1-[4,5-dihydroxy-N2-(10,12-dimethyl-1-oxotetradecyl)-ornithine]-2-serine-4-[3-hydroxy-4'-O-(malonic acid)-homotyrosine]-5-[3-hydroxyglutamine]-6-[3-hydroxyproline]echinocandin C as residue. The latter is purified by reverse phase chromatography using water/acetonitrile. The compound has a molecular weight of 1120.

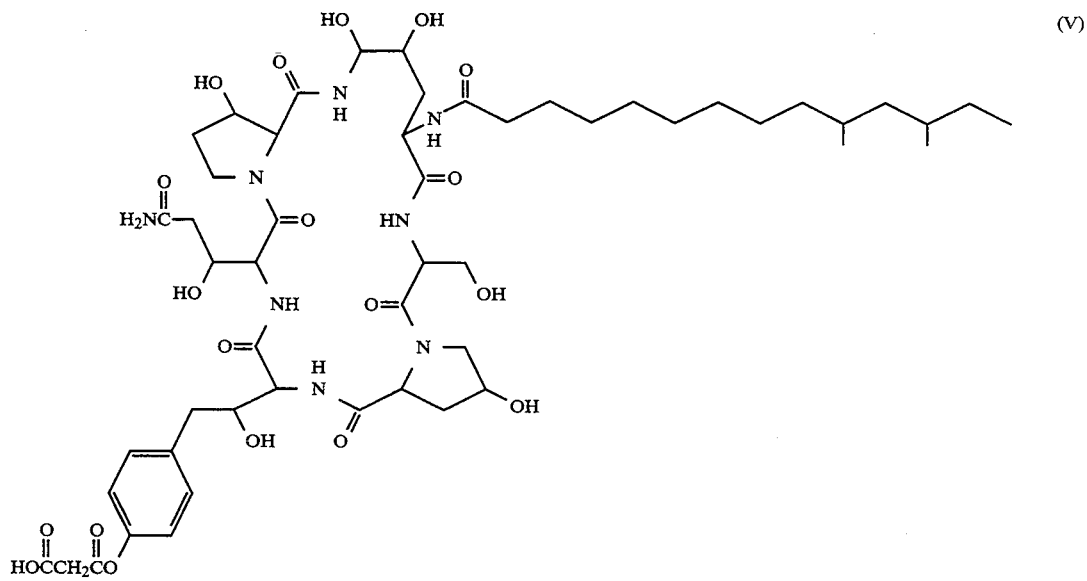

(V)

In reactions carried out in a manner similar to that described in the foregoing examples, 31 milligrams (1.1 eq) of 4-dimethylaminopyridine and 55 mg (1.1 eq) of monobenzyl malonic acid chloride are added sequentially to a solution of 250 milligrams (0.234 mmol) of the benzyl ether of Z-2(DMTD) in 2.5 ml of dry pyridine

EXAMPLE VI

1-[4,5-dihydroxy-N2-(10,12-dimethyl-1-oxotetradecyl)ornithine]-2-serine-4-[3-hydroxy-4'-O-(2-carbamoylacetic acid)-homotyrosine]-5-[3-hydroxyglutamine]-6-[3-hydroxyproline]echinocandin C

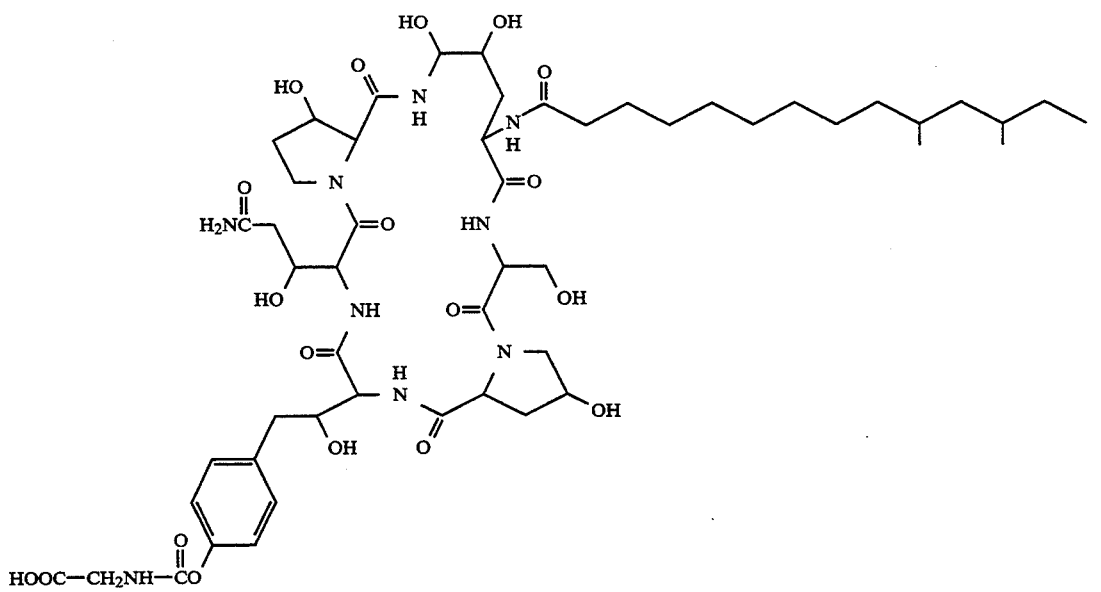

(VI)

77/AOR43 -38 -18134

In a manner similar to that described in Example I, 350 mg of Compound Z-2 (DMTD) is suspended in 7 ml of tetrahydrofuran and to the suspension is added 0.68 ml of benzyl alcohol, 3 ml of dimethylformamide and 7 ml of p-toluenesulfonic acid and the resulting mixture stirred for 24 hours at room temperature. At the end of this period, the volatiles are removed in vacuo and the residue obtained purified by preparative HPLC using water/acetonitrile as eluant. The appropriate fractions are combined and lyophilized to obtain the benzyl ether, 1-[4-hydroxy-5-benzyloxy-N2-(10,12-dimethyl-1-oxotetradecyl)-ornithine]-2-serine-4-[3-hydroxyhomotyrosine]-5-[3-hydroxyglutamine]-6-[3-hydroxyproline]echinocandin C.

To a solution of 269 mg (0.234 mmol) of the benzyl ether of Compound Z-2 (DMTD) in 2.5 ml of dry pyridine is added sequentially 31 mg (1.1 eq) of 4-dimethylaminopyridine and 50 mg (1.1 eq) of benzyl-2-isocyanatoacetic acid and the resulting mixture stirred at room temperature for several hours. At the end of the this period, the mixture is concentrated in vacuo, taken up in water/acetonitrile and purified using reverse phase chromatography (1 inch diameter "Zorbax" C8 column) and eluted with water/acetonitrile. Fractions containing the desired material as determined by HPLC assay are concentrated in vacuo to remove acetonitrile and then lyophilized to obtain purified benzyl carbamate.

In a manner similar to that described in Examples I and II, 250 mg (0.2 mmole) of the benzyl carbamate benzyl ether of Z-2 (DMTD) is dissolved in 15 ml of absolute ethanol. Next, 200 mg of 10% Pd-C is added and the mixture stirred under 1 atmosphere of hydrogen at room temperature for about 5 hours. The resulting mixture is then filtered, the filtrate concentrated to obtain the desired 1-[4,5-dihydroxy-N2-(10,12-dimethyl-1-oxotetradecyl)-ornithine]-2-serine-4-[3-hydroxy-4'-O-(2-carbamoylacetic acid)homotyrosine]-5-[3-hydroxyglutamine]-6-[3-hydroxyproline]echinocandin C as residue. The product is purified by reverse phase chromatography (1 inch diameter "Zorbax" C8 column) eluting with water/acetonitrile.

The compound has a molecular weight 1149.

EXAMPLE VII

1-[4,5-Dihydroxy-N2-(10,12-dimethyl-1-oxotetradecyl)ornithine]-2-serine-4-[3-hydroxy-4'-O-(glycyl)-homotyrosine]-5-[3-hydroxyglutamine]-6-[3-hydroxyproline]echinocandin C

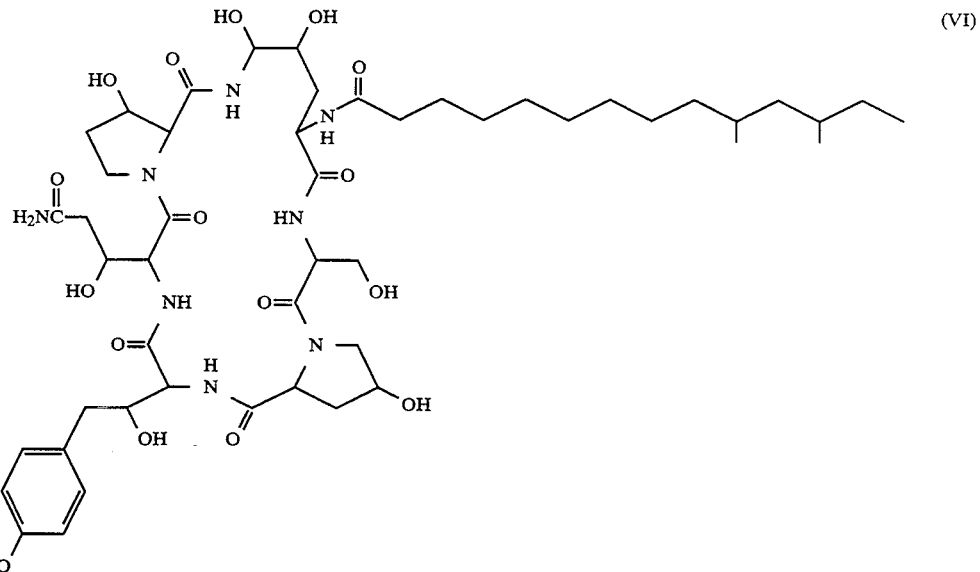

(VI)

In a manner similar to that previously described, 31 milligrams (1.1 eq) of 4-dimethylaminopyridine and 126 milligrams (1.1 eq) of N-carboxybenzylglycine symmetrical anhydride are added sequentially to a solution of 250 milligrams (0.234 mmol) of the benzyl ether of Z-2(DMTD) in 2.5 milliliters of dry pyridine and the mixture stirred at room temperature for 8 hours. It is then concentrated in vacuo, the residue dissolved in water/acetonitrile and purified by preparative reverse phase chromatography, eluting with water/acetonitrile.

The fractions containing the desired material are combined and concentrated, and then lyophilized to obtain purified carboxybenzyl protected glycyl ester, 1-[4-hydroxy-5-benzyloxy-N 2-(10,12-dimethyl-1-oxotetradecyl)-ornithine]-2-serine-4-[3-hydroxy-4'-O-(N-carboxybenzylglycyl)homotyrosine]-5-[3-hydroxyglutamine]-6-[3-hydroxyproline]echinocandin C.

The ester thus obtained is dissolved in 12 milliliters of ethanol containing an excess of anhydrous hydrochloric acid and 20 milligrams of 10% Pd-C catalyst is added and hydrogenation carried out at 1 atmosphere for 5 hours. At this time the catalyst is filtered off and the filtrate concentrated to recover the 1-[4,5-dihydroxy-N2-(10,12-dimethyl-1-oxotetradecyl)-ornithine]-2-serine-4-[3-hydroxy-4'-O-(glycyl)-homotyrosine]-5-[3-hydroxyglutamine]-6-[3-hydroxyproline]echinocandin B hydrochloride product. The product has a molecular weight of 1127.5 as the hydrochloride salt.

EXAMPLE VIII

In similar operations, the following compounds are prepared:

| Compound No. | R'' | R''' | R | R' |
|---|---|---|---|---|
| VIII | $CH_3$ | $CH_3$ | $SO_3H$ | DMTD |
| IX | $CH_3$ | $CH_3$ | $\overset{O}{\underset{\|}{P}}(ONa)_2$ | DMTD |
| X | $CH_3$ | H | $\overset{O}{\underset{\|}{P}}(ONa)_2$ | $-(CH_2)_7CH=CH(CH_2)_5CH_3$ |
| XI | $CH_3$ | H | $SO_2ONa$ | DMTD |
| XI | $CH_3$ | H | $COCH_2COOH$ | $-C_{17}H_{35}$-n |
| XII | $CH_3$ | H | $CONH(CH_2)_2COOH$ | DMTD |
| XIII | $CH_3$ | H | $CO(CH_2)_2NH_2.HCl$ | DMTD |
| XIV | $CH_3$ | H | $CONH(CH_2)_2NH_2.HCl$ | $C_{13}H_{27}$-n |
| XV | $CH_3$ | H | $\overset{O}{\underset{\|}{P}}(OH)_2$ | $-(CH)_7CH=CH(CH_2)_5CH_3$ |
| XVI | $CH_3$ | H | $COOCH_2COOH$ | $-C_{15}H_{31}$-n |
| XVII | $CH_3$ | H | $CON(CH_3)(CH_2)_2COOH$ | $-C_6H_4-S-C_6H_{13}$-n |
| XVIII | $CH_3$ | H | $COCH(CH_2C_6H_5)NH_2.HCl$ | DMTD |
| XIX | $CH_3$ | H | $COCH_2NH_2.HCl$ | DMTD |

-continued

| Compound No. | R'' | R''' | R | R' |
|---|---|---|---|---|
| XX | CH$_3$ | H | COOCH$_2$NH$_2$.HCl | —C$_6$H$_4$OC$_8$H$_{17}$-n |

In the following examples "Compound" followed by a Roman numeral designation refer to the compound in the example corresponding to the Roman numeral.

EXAMPLE IX 1000 compressed tablets each containing 500 mg of Compound I of Example I are prepared from the following formulation:

| Compound | Grams |
|---|---|
| Compound I | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE X 1000 hard gelatin capsules, each containing 500 mg of the sodium salt of compound of Example II are prepared from the following formulation:

| Compound | Grams |
|---|---|
| Compound II | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE XI 1000 hard gelatin capsules, each containing 500 mg of Compound are prepared from the following formulation:

| Compound | Grams |
|---|---|
| Compound A-1a | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XII 1000 hard gelatin capsules, each containing 500 mg of Example III ("Compound III") are prepared from the following formulation:

| Compound | Grams |
|---|---|
| Compound III | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XIII 250 ml of an injectable solution are prepared by conventional procedures having the following formulation:

| Dextrose | 12.5 g |
|---|---|
| Water | 250 mL |
| Compound I | 400 mg |

The ingredients are blended and thereafter sterilized for use.

EXAMPLE XIV 250 ml of an injectable solution are prepared by conventional procedures having the following formulation:

| Dextrose | 12.5 g |
|---|---|
| Water | 250 ml |
| Compound II | 400 mg |

The ingredients are blended and thereafter sterilized for use.

EXAMPLE XVII

An ointment suitable for topical application may be prepared by intimately dispersing 13 mg of Compound II in 1 g of commercially available polyethylene/hydrocarbon gel.

EXAMPLE XVI

An injectable solution is prepared similar to that of Example XIII except that Compound IV is substituted for Compound I.

EXAMPLE XVII 1000 hard gelatin capsules, each containing 500 mg of Compound II are prepared from the following formulation:

| Compound | Grams |
|---|---|
| Compound II | 500 |
| Starch | 250 |
| Lactose | 750 |
| Talc | 250 |
| Calcium Stearate | 10 |

The components are uniformly blended and used to fill two-piece hard gelatin capsules.

EXAMPLE XVIII

An aerosol composition may be prepared having the following formulation:

|  | Per Canister |
| --- | --- |
| Compound I | 24 mg |
| Lecithin NF Liquid Concentrated | 1.2 mg |
| Trichlorofluoromethane, NF | 4.026 g |
| Dichlorodifluoromethane, NF | 12.15 g |

Starting Materials

The starting three lipopeptides are natural products which may be produced by the cultivation of a fungus of the genus Cryptosporiopsis as described in PCT patent application WO 82/00587 and also reported by W. Pache et al in Abstracts of the 13th International Congress Chemotherapy (1983), PS 48/3, Part 115, Abstract No. 10 (Ann. Reports in Medicinal Chemistry, Vol 19, Ch 13, p. 130 Academic Press, 1984)

What is claimed is:

1. A compound having the formula:

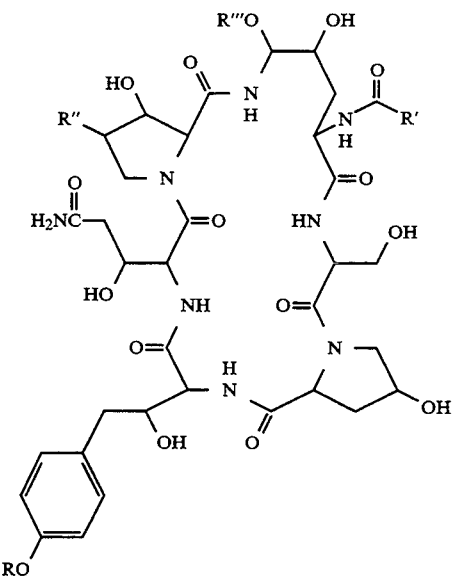

wherein

R is acyl, phosphono or sulfo radical which possesses a charged group at neutral pH;

R' is a $C_5$–$C_{23}$ alkyl, $C_5$–$C_{23}$ alkenyl or $C_5$–$C_{23}$ alkynyl or aryl R" and R"' are independently H or $CH_3$ and selected from those in which (1) R" is $CH_3$ and R"' is H (2) R" and R"' are both H; and (3) R" and R"' are $CH_3$.

2. A method for treating mycotic infections in patients in need of therapy comprising administering a therapeutically effective amount of a compound of claim 1.

3. A method for preventing or treating Pneumocystis carinii infections in immune comprised patients which comprises administering a preventative or therapeutically effective amount of the compound of claim 1.

4. An antimicrobial composition comprising a compound of claim 1 in admixture with a biologically inert carrier.

5. A compound having the formula

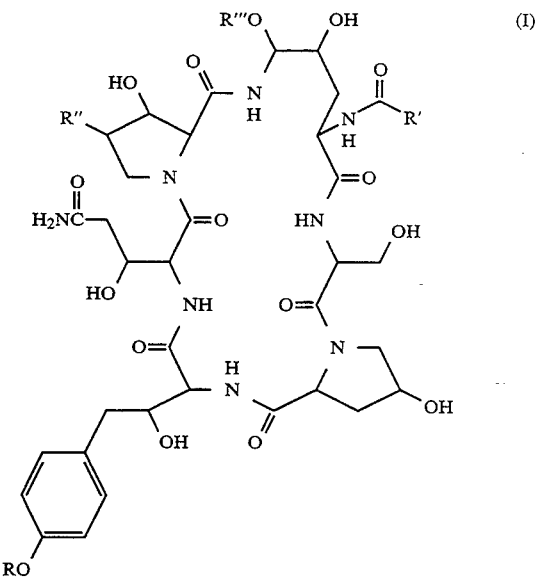

wherein

R' is $C_5$–$C_{23}$ alkyl, $C_5$–$C_{23}$ alkenyl, $C_5$–$C_{23}$ alkynyl or aryl; and R is (1) $PO_3AH$ wherein A is H, $C_1$–$C_6$ alkyl, phenyl or substituted phenyl wherein the substituent may be alkyl, alkyloxy, alkylthio, or alkylamino or a Li, Na, K, Mg and Ca cation salt thereof;

(2) $SO_3H$ or cation salt thereof as defined in (1);

(3) $COC_nH_{2n}CO_2H$ wherein n is 1 to 6 or a cation salt thereof as defined in (1);

(4) $CONAC_nH_{2n}CO_2H$ wherein A is as defined in (1), n is 1 to 6, or a cation salt thereof as defined in (1);

(5) $COOC_nH_{2n}CO_2H$ wherein n is 1 to 6, or a cation salt thereof as defined in (1);

(6) $CONA(CHB)CO_2H$ wherein B is a residue of an amino acid, or a cation salt thereof as defined in (1);

(7) $COCHBNR_1R_2$ wherein B is a residue of an amino acid, $R_1$ and $R_2$ independently are H, $C_1$–$C_6$ alkyl, and phenyl, and acid addition salts thereof;

(8) $CONAC_nH_{2n}NR_1R_2$ wherein A is as defined in (1), $R_1$ and $R_2$ independently are as defined in (7), n is 2 to 6, and acid addition salts thereof;

(9) $COOC_nH_{2n}R_1R_2$ wherein $R_1$ and $R_2$ independently are as defined in (7), n is 2 to 6, and acid addition salts thereof; and

(10) $COC_nH_{2n}NR_1R_2$ wherein $R_1$ and $R_2$ independently are as defined in 6, n is 1 to 6 and acid addition salts thereof.

R" and R"' are independently H or $CH_3$ and selected from those in which (1) R" is $CH_3$ and R"' is H (2) R" and R"' are both H; and (3) R" and R"' are $CH_3$.

6. A compound according to claim 2 wherein, R is phosphono and R' is 9,11-dimethyltridecyl and R" is $CH_3$ and R"' is H.

7. A compound according to claim 2 in which, R is phosphono and R' is 9,11-dimethyltridecyl and R" and R"' are H.

* * * * *